United States Patent [19]

Fischer et al.

[11] Patent Number: 4,942,992
[45] Date of Patent: Jul. 24, 1990

[54] GLOVE DISPENSER

[76] Inventors: Frank E. Fischer, 7500 Bellerive #1419, Houston, Tex. 77036; Shayne A. Kelly, 2502 Long Reach, Sugarland, Tex. 77478

[21] Appl. No.: 428,962
[22] Filed: Oct. 30, 1989
[51] Int. Cl.⁵ .......................... B65D 81/00; A45F 5/02
[52] U.S. Cl. ..................................... 224/240; 224/245; 224/247; 224/253; 224/904; 224/914
[58] Field of Search .............. 224/253, 236, 240, 242, 224/245, 914, 904, 247; 24/3 J, 3 L; 8/160, 161 R; 206/282, 284, 285, 604, 292, 295, 297; 223/111, 112

[56] References Cited

U.S. PATENT DOCUMENTS

| | | | |
|---|---|---|---|
| 1,518,092 | 12/1924 | Meegan | 224/252 |
| 4,069,913 | 1/1978 | Harrigan | 206/278 |
| 4,099,614 | 7/1978 | Heissenberger | 206/299 |
| 4,155,494 | 5/1979 | Poncy et al. | 223/111 |
| 4,476,588 | 10/1984 | Long | 2/169 |
| 4,515,270 | 5/1985 | Alvarado | 206/438 |
| 4,567,065 | 1/1986 | Schneiderman | 427/230 |
| 4,689,935 | 9/1987 | Harding | 53/431 |
| 4,773,532 | 9/1988 | Stephenson | 206/278 |
| 4,844,293 | 7/1989 | McLaughlin | 221/34 |
| 4,852,783 | 8/1989 | Bryden et al. | 224/240 |

Primary Examiner—Henry J. Recla
Assistant Examiner—David J. Walczak
Attorney, Agent, or Firm—Harrison & Egbert

[57] ABSTRACT

A glove dispenser comprising a case and a clip fastened to the case. The case has an open position and a closed position. A belt loop is formed on the back surface of the case so as to allow the case to be attached to a belt. The clip is fastened to the case so as to receive the cuff of a glove. The case comprises a back panel, and a connector on the back panel for releasably affixing the front panel in close proximity to the back panel. The clip is interposed between the back panel and the front panel. The clip is a member having a first portion affixed to the case and a second portion in torsional abutment with the first portion. The front panel includes a pocket formed therein for the receipt of additional disposable gloves.

20 Claims, 3 Drawing Sheets

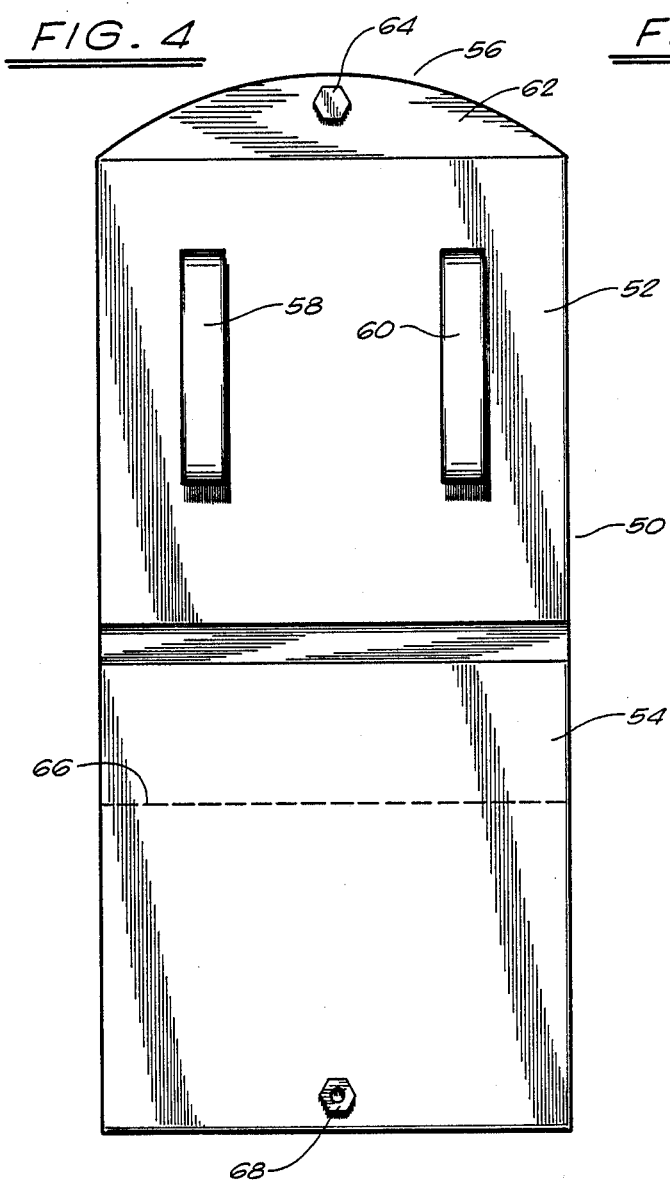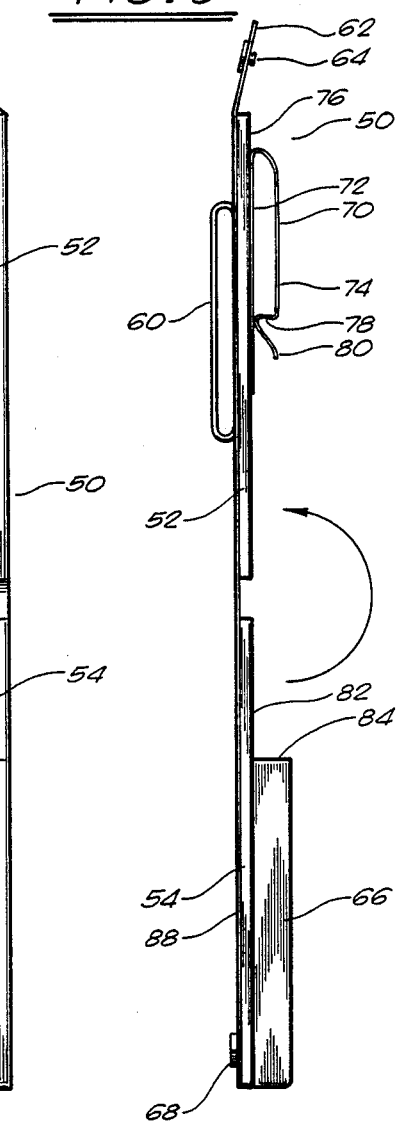

GLOVE DISPENSER

TECHNICAL FIELD

The present invention relates to dispensers of gloves. More particularly, the present invention relates to dispensers of disposable gloves for police use.

BACKGROUND ART

In the field of police work, it is often necessary to apprehend criminals, vagrants, or other persons. Many times, such persons are of an extremely unsanitary condition. In other situations, the person being apprehended may be bloody and/or carry a contagious disease. Policemen are very concerned about the avoidance of contagious disease during the apprehension of such individuals. In addition, it is often unpleasant to have direct flesh-to-flesh contact with dirty and filthy individuals.

In the course of the apprehension of the criminal, the police officer must use one hand to immobilize such criminal. Typical immobilization occurs when the police officer asks the criminal to face a wall and to place his hands on the wall. During this time the police officer needs to maintain one hand in direct contact with the person so that the person cannot move without the police officer's knowledge. Alternatively, the police officer may have his gun drawn with one hand. It is also necessary that the officer keep his eyes on the person during the entire time that such criminal is immobilized.

It is desirable that officers wear some protection against contagious disease. It is also desirable that the officer be able to don such protection without the need to divert his attention from the criminal. As such, it is very desirable that the police officer be able to place a disposable glove on his hand through a non-visual one-handed operation.

Various U.S. patents have issued that describe disposable glove dispensing apparatus. U.S. Pat. No. 4,844,293, issued on July 4, 1989, to D. T. McLaughlin, describes a dispensing apparatus for disposable gloves which is a box-like, rectangular enclosure for housing a removably mounted packet containing a plurality of disposable gloves arranged in the packet in closely spaced, planar unfolded condition. The packet of gloves is loaded into the enclosure through a top opening. The gloves are disposed so that they may be removed, one at a time, through the front opening of the enclosure.

U.S. Pat. No. 4,773,532, issued on Sept. 27, 1988, to M. Stephenson, describes a dispensing system for sterile gloves. In this invention, a multitude of flattened sterile surgical gloves are provided in a roll form. The roll is in a continuous spirally wound impervious backing sheet having uniformly spaced parallel transverse tear lines. The gloves are attached by adhesive to the sheet between the tear lines. The cuff portions are upwardly directed. Structure is associated with the cuff portion to cause the glove to automatically open at the cuff, thereby facilitating insertion of a hand into the glove.

U.S. Pat. No. 4,069,731, issued on Jan. 24, 1978, to Roy M. Harrigan, discloses a surgical glove package and fixture. The wrist portion of the glove is releasably fastened around a glove ring member, with the hand portion of the glove extending from the ring member. An outer, imperforate, flexible member encloses the surgical glove. The wrist portion of the glove extends through the ring member and is folded over and stretched around the ring member. The outer protective member also extends around the ring member and passes between the stretched wrist portion and the ring member. In this configuration, the user is able to place the glove over a single hand with a one-handed operation.

U.S. Pat. No. 4,155,494, issued on May 22, 1979, to Poncy et al., describes a donning system for surgical gloves. In this invention, the cuff of the glove is stretched around a packaging ring so that the glove cuff extends radially back toward the center of the ring. A flexible, transparent liner covers the outside surface of the glove and between the glove cuff and the ring so that the glove cuff holds the liner securely to the ring. The glove is donned and removed from the ring by using the liner to manipulate the glove package. The glove package can also be used with an inflating apparatus which inflates the glove prior to inserting a hand into the inflated glove.

None of these prior art patents is particularly adaptable to police work. Initially, these prior art patents are featured in the medical field, rather than the police field. Additionally, none of the apparatus is adaptable for usage on a belt.

It is an object of the present invention to provide a glove dispensing apparatus that allows the user to attach the glove in a one-handed procedure.

It is another object of the present invention to provide a glove dispensing apparatus that is suitable for attachment to the belt of a police officer.

It is still another object of the present invention to provide a glove dispenser that allows the user to easily attach the glove without visual observation.

It is still another object of the present invention to provide a glove dispenser that is relatively inexpensive, easy to use, and simple to install.

These and other objects and advantages of the present invention will become apparent from a reading of the attached specification and appended claims.

SUMMARY OF THE INVENTION

The present invention is a glove dispenser that comprises a case having an open position and a closed position and a clip that is fastened to the case for receiving the cuff of a glove. The case includes suitable attachment members so as to allow the case to be connected to a belt.

The case of the present invention comprises a back panel having the belt-attachment member connected to one side, a front panel that is foldably connected to the back panel, and a connector on the back panel for releasably attaching the front panel in close proximity to the back panel. The connection of the front panel in close proximity to the back panel establishes the closed position of the case. The releasing of the front panel from the back panel causes the case to open in a relatively flat arrangement so as to expose the glove. The clip is interposed between the back panel and the front panel. The attachment member for allowing the case to be connected to a belt includes a first loop that extends vertically and is fastened to the backside of the case, and a second loop that extends vertically and is parallel to the first loop.

The clip is a metallic member having a first portion that is affixed to the case and a second portion in torsional abutment with the first portion. The area of abutment between the first portion and the second portion is the area that receives the cuff of the glove. When suitable pressure is applied to this torsional abutment, the first portion will separate from the second portion so as to allow the release of the glove. Alternatively, the glove may be pulled so as to slide between the first portion and the second portion. When the case is in the closed position, the disposable glove is contained within the case.

The connector is a button that is affixed to a flap. The flap is in foldable relation to the back panel. The front panel has a socket for the button that is affixed so that the socket snap-fits to the button when the case is in its closed position. The flap is connected to one end of the back panel and the front panel is connected to the other end of the back panel. The front panel includes a pocket that is formed therein for the receipt of additional surgical gloves.

Ideally, the clip should have a width of greater than three/quarters (¾) of an inch. The surgical glove is received by the width of the clip and extends across the width of the clip. This width is necessary so that the proper opening of the cuff of the glove is established.

BRIEF DESCRIPTION OF THE DRAWINGS

FIG. 4 is a rearward view of the open case of an alternative embodiment of the present invention.

FIG. 5 is a side view of the alternative embodiment of FIG. 4.

DETAILED DESCRIPTION OF THE INVENTION

Figure 1:
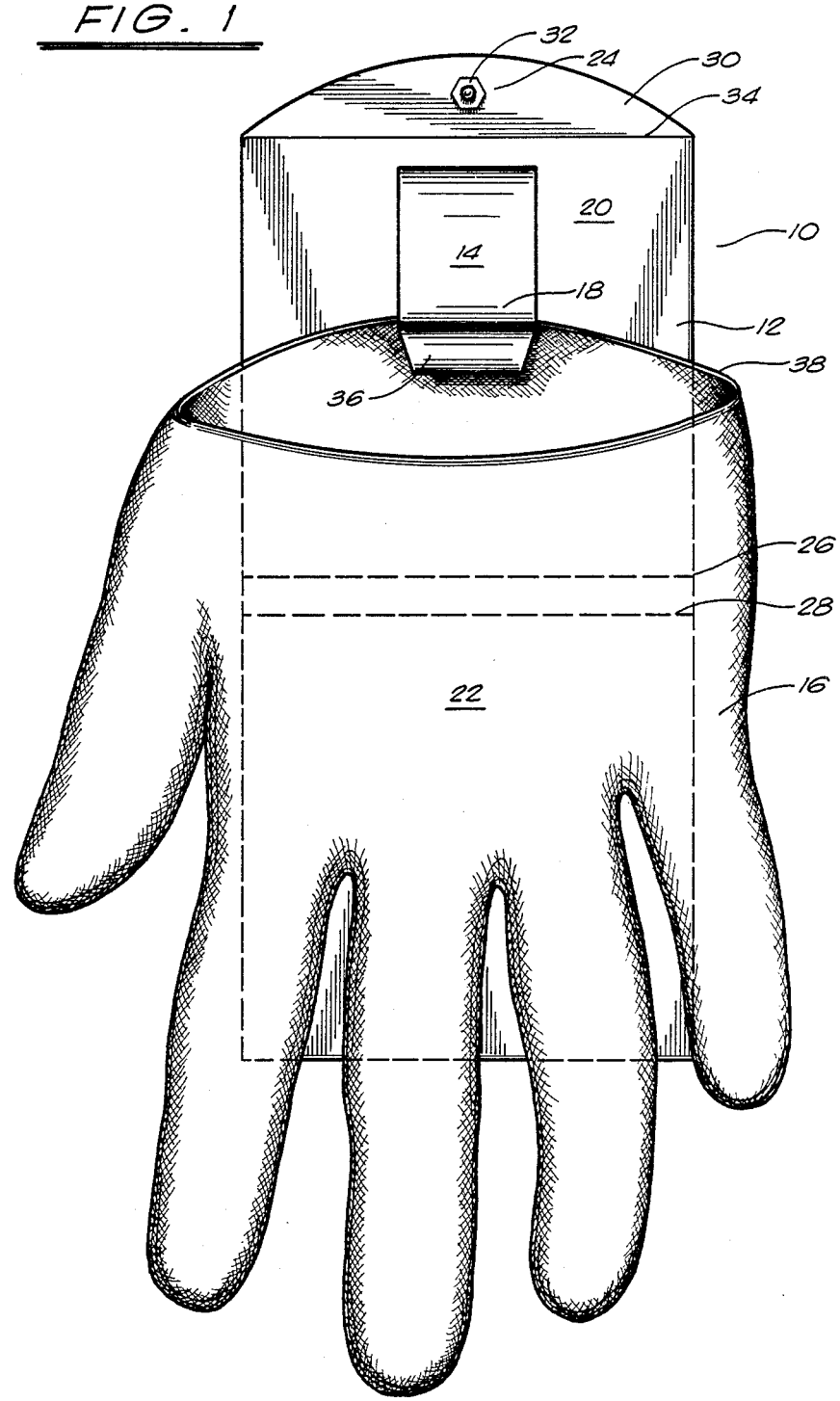
FIG. 1 is an illustration of the preferred embodiment of the present invention showing the case in its open position with glove properly exposed.

Referring to FIG. 1, there is shown at 10, the glove dispenser in accordance with the preferred embodiment of the present invention. Glove dispenser 10 comprises case 12, clip 14, and disposable glove 16. The glove 16 is received by the end portion 18 of clip 14. Clip 14 is affixed to the surface of case 12. Although not shown in FIG. 1, case 12 has suitable means for the attachment of case 12 to a belt.

Case 12 includes a back panel 20, a front panel 22 (shown in partial dotted line), and a connector 24. The front panel is foldably connected at score lines 26 and 28 to the back panel 20. Typically, the front panel 22 and the back panel 20 will be comprised of a leather material. Although it is preferable that the panels 20 and 22 be of a leather material, this is not intended to be limitation on the present invention It is believed that any somewhat flexible material will be appropriate for the formation of panels 20 and 22. Score lines 26 and 28 allow the front panel 22 to fold and rotate relative to the back panel 20. In the configuration illustrated in FIG. 1, panels 20 and 22 are generally aligned vertically. The position indicated in FIG. 1 is the open position of the case 12.

Connector 24 includes flap 30 and button 32. Flap 30 is foldably connected at score line 34 to the back panel 20. Button 32 is affixed to the flap 30 in generally the central portion of flap 30. Button 32 is of a type that engages a suitable socket attached to the front panel 22. As can be seen in FIG. 1, flap 30 can rotate upwardly so as to be aligned with the back panel 20 and the front panel 22.

Clip 14 is a metallic member that is rigidly affixed to the surface of back panel 20. Clip 14 extends downwardly to the trapezoidal end portion 36. Clip 14 has a first portion that is in torsional abutment with a surface on back panel 20. Glove 16 includes a cuff 38 that is received by the clip 14. The pressurized abutment of the end 36 of clip 14 will cause the glove 16 to be releasably fixed in the position indicated in FIG. 1. The width of clip 14 should be greater than three-quarters of an inch. The cuff 38 of disposable glove 16 extends for the width of clip 14. This width of the clip is important so as to allow the cuff 38 to be sufficiently expanded for one-handed, non-visual insertion of a hand. If the clip 14 had a smaller width, than it is likely that the cuff 38 of glove 16 would remain closed and difficult to attach. Additionally, the width of clip 14 will prevent the glove 16 from being subjected to tearing, puncture, or ripping during hand insertion.

FIG. 1 shows the glove 16 in its fully expanded configuration. This is the appearance of the glove 16 when the front panel 22 is released from back panel 20. Upon the releasing of connector 24, the glove 16 will drop, along with front panel 22, so as to be open for access. In usage, the police officer may insert his hand into cuff 38. After the police officer's hand is inserted in cuff 38, additional pulling will cause the cuff 38 to slide from the engagement area of clip 14. After this procedure is completed, the glove 16 should be suitably fitted to the hand of the user.

Figure 2:
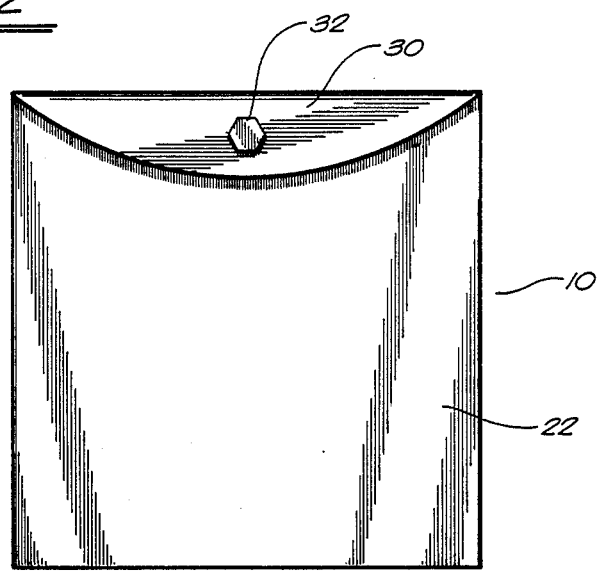
FIG. 2 illustrates the case of the present invention in its closed position.

FIG. 2 shows the glove dispenser 10 in its closed position. In FIG. 2, it can be seen that the front panel 22 is in close juxtaposition with the back panel of glove dispenser 10. Flap 30 is folded over the end of the front panel 22 such that the button 32 engages a socket on the front panel 22. Glove 16 is folded within the glove dispenser 10 so that the glove does not protrude from the edges of the glove dispenser 10. In the configuration illustrated in FIG. 2, the glove dispenser 10 may be attached to the belt of a police officer, or other user, so as to be ready for use. When use is necessary, the police officer may pull on flap 30 so as to release button 32 from the socket. The front panel 22 will then automatically fall downwardly so as to assume the position illustrated in FIG. 1. The glove 16 will then drape appropriately for hand insertion.

Figure 3:
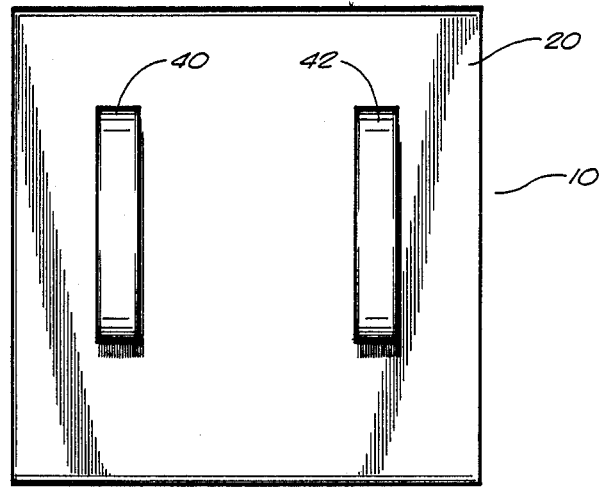
FIG. 3 shows the backside of the case with belt loops exposed.

FIG. 3 shows the backside of back panel 20. In FIG. 3, the glove dispenser 10 is also in its closed position. The backside of back panel 20 includes a first loop 40 and a second loop 42 affixed thereto. The first loop 40 extends vertically and is fastened to the back of glove dispenser 10. The second loop 42 also extends vertically and is fastened to the back panel 20 of glove dispenser 10. Loops 40 and 42 are of similar size and are aligned in parallel. Loops 40 and 42 should be of suitable size for attachment to a belt. Although FIG. 3 illustrates the use of two loops, it may be possible that a single loop may be utilized so as to attach the glove dispenser 10 to a belt.

FIG. 4 illustrates the open position of the backside of an alternative embodiment 50 of the glove dispenser. It can be seen in FIG. 4 that the alternative embodiment 50 includes the back panel 52, the front panel 54, and the connector 56 in a configuration similar to that of FIG. 1. In FIG. 4, it can be seen that belt loops 58 and 60 are attached to the back panel 52. Connector 56 includes a flap 62 and associated button 64. The front panel 54 includes, in this alternative embodiment, a pocket 66 extending across the width of the front side of front panel 54. Pocket 66 is designed to receive additional disposable gloves or to receive a used disposable glove. In FIG. 4, it can be seen that the socket 68 is fastened to the front panel 54 so as to engage the button 64 of flap 62.

FIG. 5 is a side view of the alternative embodiment 50 of FIG. 4. Importantly, FIG. 5 illustrates the configuration of clip 70. Initially, clip 70 includes a first portion 72 and a second portion 74. Clip 70 is a metallic member having sufficient torsional strength so as to maintain the disposable glove in proper position. First portion 72 is affixed and in surface-to-surface contact with the face 76 of first panel 52. This first portion 72 of clip 70 may be sewed, or adhesively fastened, to the surface 76 of back panel 52. The second portion 74 extends from first portion 72 by means of forming and bending the clip 70. First portion 74 includes an indentation 78 that extends so as to be in torsional abutment with the first portion 72. The second portion 74 then includes outwardly extending portion 80. The disposable glove will be inserted into the area of abutment between first portion 72 and second portion 74 of clip 70. The front panel 54 includes pocket 66 that is formed thereon. Pocket 66 may be appropriately sewn, or adhesively fastened, to the surface 82 of front panel 54. Pocket 66 should have a sufficient size to receive used, or additional, disposable gloves. Such gloves may be inserted into open end 84 of pocket 66. A socket 68 is fastened to the surface 88 of front panel 54. The arrow in FIG. 5 illustrates the rotational movement of the front panel 54 with respect to the back panel 52. When the front panel 54 has been rotated upwardly so as to be in close proximity to the back panel 52, the flap 62 may be rotated downwardly so as to allow button 64 to engage socket 68. In the open position illustrated in FIG. 5, the disposable glove will drape downwardly from clip 70. In the closed position, the glove will be contained in the area between the back panel 52 and the front panel 54. The glove dispenser 50 may then be attached by loop 60 to the belt of a police officer.

Glove 16 is preferably comprised of a very thin film of elastomeric material. Talcum powder may be placed within the glove so as to assist in the insertion of the hand therein. The glove includes finger and cuff portions and a suitable palm and backside. The disposable glove 16 is of a configuration commonly described as "surgical gloves", "rubber gloves", or similar names.

The present invention offers a number of advantages not found in the prior art. First, and foremost, the present invention provides a safe and hygienic technique for touching unsanitary individuals. The disposable glove prevents blood, or other contaminants, from passing onto the hand of the police officer. The present invention can save the time of the police officer since the glove may be removed and handwashing is not required. The present invention also offers a complete safeguard against blood-to-blood contact with the individual under arrest.

Another advantage of the present invention is that it will allow the police officer to insert his hand into the disposable glove without the need for visual observation or two-handed manipulation. This is important since the police officer may have to use his other hand for immobilizing the arrestee. Alternatively, the police officer may have one hand on a gun and require the other hand for insertion into the disposable glove. The police officer can also have two glove dispensers on his belt. This will allow the officer to cover both hands, if needed for an arrest.

The present invention is relatively simple to manufacture, inexpensive, and easy to use. In proper use, the police officer's belt is inserted through the loops on the back panel of the glove dispenser. To use the glove dispenser, the only motion that is required is to snap the flap so as to expose the glove. After use, the glove may be disposed of in a trash can, or may be inserted into the pocket on the front panel of the dispenser. Additional disposable gloves may be suitably compressed and inserted into the pocket for later use. As such, the present invention offers a great deal of flexibility of use.

The foregoing disclosure and description of the invention is illustrative and explanatory thereof, and various changes in the details of the illustrated apparatus can be made within the scope of the appended claims without departing from the spirit of the invention. The present invention should only be limited by the following claims and their legal equivalents.

We claim:

1. A glove dispenser comprising:
    a case having an open position and a closed position, said case having means on one side for attachment to a belt: and
    a clip within said case and fastened thereto said clip adapted for receiving the cuff of a glove.

2. The glove dispenser of claim 1, said case comprising:
    a back panel having said means for attachment to a belt attached thereto;
    a front panel foldably connected to said back panel; and
    a connector on said back panel for releasably attaching said front panel in close proximity to said back panel.

3. The glove dispenser of claim 2, said clip interposed between said back panel and said front panel.

4. The glove dispenser of claim 2, said connector having a button affixed to a flap, said flap in foldable relationship to said back panel, said front panel having a socket for said button affixed such that said socket snap-fits to said button when said case is in said closed position.

5. The glove dispenser of claim 4, said flap connected to one end of said back panel, said front panel connected to the other end of said back panel.

6. The glove dispenser of claim 2, said front panel having a pocket formed therein for the receipt of a disposable glove.

7. The glove dispenser of claim 1, said means for attachment to a belt comprising:
    a first loop extending vertically and fastened to the back of said case; and
    a second loop extending vertically and fastened to the back of said case, said first and second loops being parallel to each other.

8. The glove dispenser of claim 1, said clip comprising:
    a metallic member having a first portion affixed to said case, and a second portion in torsional abutment with said first portion, the abutment between said first portion and said second portion for receiving the cuff of a glove.

9. The glove dispenser of claim 1, further comprising:
    a disposable glove having a cuff attached to said clip, said disposable glove contained within said case, said disposable glove opening when said case is in said open position.

10. An apparatus comprising:
a case;
a clip fastened within said case; and
a disposable glove having a cuff releasably connected to said clip, said case opening such that said disposable glove opens from a folded configuration.

11. The apparatus of claim 10, said case comprising: means for the attachment of said case to a belt, said means positioned on the back surface of said case.

12. The apparatus of claim 11, said means for the attachment of said case to a belt comprising:
a first loop extending vertically and fastened to the back of said case; and
a second loop extending vertically and fastened to the back of said case, said first and second loops being parallel to each other.

13. The apparatus of claim 10, said case comprising:
a back panel;
a front panel foldably connected to said back panel; and
a connector on said back panel for releasably attaching said front panel in close proximity to said back panel.

14. The apparatus of claim 13, said clip interposed between said front panel and said back panel.

15. The apparatus of claim 13, said connector being a button affixed to a flap, said flap in foldable relation to said back panel, said front panel having a socket for said button affixed such that said socket snap-fits with said button.

16. The apparatus of claim 15, said flap connected to one end of said back panel, said front panel connected to the other end of said back panel.

17. The apparatus of claim 13, said front panel having a pocket formed therein for the receipt of a disposable glove.

18. The apparatus of claim 10, said clip exerting a compressive force so as to retain said disposable glove in position within said clip.

19. The apparatus of claim 18, said clip having a first portion rigidly affixed to said case, said clip having a second portion in torsional abutment with the surface of said first portion.

20. An apparatus comprising:
a case;
a clip fastened to said case, said clip having a width of greater than three-quarters of an inch; and
a disposable glove having a cuff releasably connected to said clip, said disposable glove extending across the width of said clip, said case opening such that said disposable glove opens from a folded configuration.

* * * * *